US010506326B2

(12) United States Patent
Prevoir et al.

(10) Patent No.: US 10,506,326 B2
(45) Date of Patent: Dec. 10, 2019

(54) WEARABLE DEVICES WITH INCREASED ADHESION

(71) Applicant: Bose Corporation, Framingham, MA (US)

(72) Inventors: Shawn J. Prevoir, Northborough, MA (US); Kai Gao, Marlborough, MA (US)

(73) Assignee: Bose Corporation, Framingham, MA (US)

(*) Notice: Subject to any disclaimer, the term of this patent is extended or adjusted under 35 U.S.C. 154(b) by 0 days.

(21) Appl. No.: 15/967,994

(22) Filed: May 1, 2018

(65) Prior Publication Data
US 2018/0376236 A1  Dec. 27, 2018

Related U.S. Application Data
(60) Provisional application No. 62/500,596, filed on May 3, 2017.

(51) Int. Cl.
  H04R 1/10      (2006.01)
  A61B 5/00      (2006.01)
  A61B 5/024     (2006.01)

(52) U.S. Cl.
  CPC .......... *H04R 1/1066* (2013.01); *H04R 1/105* (2013.01); *H04R 1/1016* (2013.01); *H04R 1/1091* (2013.01); *A61B 5/024* (2013.01); *A61B 5/683* (2013.01); *A61B 5/6817* (2013.01); *H04R 2460/17* (2013.01)

(58) Field of Classification Search
  CPC .... H04R 1/1066; H04R 1/1016; H04R 1/105; H04R 1/1091; H04R 2460/17; A61B 5/024; A61B 5/6817; A61B 5/683
  USPC ........................................................ 381/380
  See application file for complete search history.

(56) References Cited

U.S. PATENT DOCUMENTS

| 2010/0217102 | A1* | 8/2010 | LeBoeuf | A61B 5/00 600/310 |
| 2013/0019374 | A1 | 1/2013 | Schwartz | |
| 2013/0131519 | A1* | 5/2013 | LeBoeuf | A61B 5/0077 600/476 |
| 2016/0324478 | A1 | 11/2016 | Goldstein | |

FOREIGN PATENT DOCUMENTS

| WO | WO 2009/117456 | 9/2009 |
| WO | WO 2013/108154 | 7/2013 |
| WO | WO 2015/179975 | 12/2015 |

OTHER PUBLICATIONS

Golnaz Dianat et al: "Vapor Phase Fabrication of Hydrophilic and Hydrophobic Asymmetric Polymer Membranes", Macromolecular Materials and Engineering., vol. 301, No. 9, Sep. 1, 2016 (Sep. 1, 2016), pp. 1037-1043, XP055496293, DE ISSN: 1438-749.
International Search Report & Written Opinion; PCT/US2018/030401; Nov. 13, 2018; 28 pages.
(Continued)

Primary Examiner — Sean H Nguyen
(74) Attorney, Agent, or Firm — Fish & Richardson P.C.

(57) ABSTRACT

Headphone ear tips are made with an outer surface that changes its coefficient of friction. The outer surface is coated with photochromic compound, hierarchical microstructures, fibers formed through electrostatic flocking, or a combination thereof.

16 Claims, 11 Drawing Sheets

(56) References Cited

OTHER PUBLICATIONS

Pamela Tannouri et al: "A Photoresponsive Biomimetic Dry Adhesive Based on Doped PDMS Microstructures", Chemistry of Materials, vol. 26, No. 15, Jul. 25, 2014 (Jul. 25, 2014), pp. 4330-4333, XP055427988, ISSN: 0897-4756.

Scott Seidel et al: "Formation of Porous Polymer Coatings on Complex Substrates Using Vapor Phase Precursors", Macromolecular Materials and Engineering., vol. 301, No. 4, Apr. 1, 2016 (Apr. 1, 2016), pp. 371-376, XP055496260, DE ISSN: 1438-7492.

Scott Seidel et al: "Simultaneous Polymerization and Solid Monomer Deposition for the Fabrication of Polymer Membranes with Dual-Scale Porosity", Macromolecules, vol. 46, No. 8, Apr. 5, 2013 (Apr. 5, 2013), pp. 2976-2983, XP055496306, US ISSN: 0024-9297.

Li, et al.; "Noninvasive and Reversible Cell Adhesion and Detachment via Single-Wavelength Near-Infrared Laser Mediated Photoisomerization"; J. Am. Chem. Soc. 2015, 137, 8199-8205.

Yang, et al.; "Salt-Responsive Zwitterionic Polymer Brushes with Tunable Friction and Antifouling Properties"; Langmuir, 2015, 31 (33), pp. 9125-9133).

Klajn; "Spiropyran-based dynamic materials"; Chem. Soc. Rev., 2014, 43, 148-184.

Chung, et al., "Preparation of Porous Membranes Grafted with Poly(spiropyran-containing methacrylate) and Photocontrol of Permeability"; J. Appl. Polym. Sci., 1994, 51, 2027-2033).

Y. Bardavid, et al., "Dipole Assisted Photogated Switch in Spiropyran Grafted Polyaniline Nanowires"; J. Phys. Chem. C, 2011, 115, 3123-3128.

Moniruzzaman, et al., "Photoresponsive polymers: An investigation of their photoinduced temperature changes during photoviscosity measurements"; Polymer, 2007, 48, 255-263.

Ratner, et al., "Photochromic Polysulfones. 2. Photochromic Properties of Polymeric Polysulfone Carrying Pendant Spiropyran and Spirooxazine Groups"; Ind. Eng. Chem. Res., 1996, 35, 1307-1315.

Warshawsky, et al., "Photochromic Polysulfones. 1. Synthesis of Polymeric Polysulfone Carrying Pendant Spiropyran and Spirooxazine Groups"; Ind. Eng. Chem. Res., 1995, 34, 2825-2832).

Allcock, et al., "Photochromic Polyphosphazenes with Spiropyran Units"; Macromolecules, 1991, 24, 2846-2851.

Oh, et al., "Spiropyran-Conjugated Pluronic as a Dual Responseive Colorimetric Detector"; Macromol. Rapid Commun., 2012, 33, 1958-1963).

Hauser, et al., "Reversible photochromism of polynorbornenes bearing spiropyran side groups" Monatsh. Chem., 2012, 143, 1551-1558.

Gushiken et al. "Fast Decoloration of Spironaphthooxazine Bound to a Poly(dimethylsiloxane) Network"; Photobiol. Sci., 2010, 9, 162-171.

Keum, et al., "The synthesis and spectroscopic properties of novel, photochromic indolinobenzospiropyran-based homopolymers prepared via ring-opening metathesis polymerization"; Dyes Pigm., 2010, 86, 74-80.

* cited by examiner

WEARABLE DEVICES WITH INCREASED ADHESION

BACKGROUND

This disclosure relates to wearable devices with machine-to-skin contact, such as ear tips for headphones, and in particular, ear tips that have material with increased adhesion (e.g., improved grip) to skin.

SUMMARY

In general, in one aspect, this disclosure is directed to an apparatus including:
a human-interface component of a wearable device, the component having an outer surface shaped to contact a portion of the body of a user, wherein:
  (i) the outer surface is coated with hierarchical microstructures, formed through chemical vapor deposition;
  (ii) the outer surface is coated with hierarchical microstructures, formed through chemical vapor deposition; wherein the microstructures are coated with a photochromic compound that is a zwitterion in its open form;
  (iii) the outer surface is coated with a photochromic compound that is a zwitterion in its open form;
  (iv) the component is made from a composition comprising a photochromic compound that is a zwitterion in its open form; or
  (v) the outer surface is coated with fibers, formed through electrostatic flocking;
or a combination thereof.
The microstructures, photochromic compound, fibers, or a combination thereof, can provide the outer surface of the component with increased adhesion.

In one aspect, the human-interface component is an ear tip having an outer surface shaped to contact a portion of the body of a user, wherein the ear tip is for use with a headphone, and the ear tip comprises an elastomer. Examples of elastomer include silicone, polynorbornene, fluoroelastomer, styrenic-based thermoplastic elastomer, polyacrylates, hydrogenated nitrile rubber, or shape-memory polymers, or a mixture thereof. The shape-memory polymer can be polyurethane.

In one aspect, the outer surface of the ear tip is coated with hierarchical microstructures, formed through chemical vapor deposition.

In another aspect, the outer surface of the ear tip is coated with hierarchical microstructures, formed through chemical vapor deposition; wherein the microstructures are coated with a photochromic compound that is a zwitterion in its open form.

Yet in another aspect, the outer surface of the ear tip is coated with a photochromic compound that is a zwitterion in its open form.

In a further aspect, the ear tip is made from a composition comprising a photochromic compound that is a zwitterion in its open form.

Yet in a further aspect, the outer surface of the ear tip is coated with a photochromic compound that is a zwitterion in its open form, wherein the photochromic compound on the outer surface is the same or different from the photochromic compound of the composition used to make the ear tip.

The photochromic compound described herein can be a spiropyran, spirooxazine, or spirodihydroindolizine. The photochromic compound in its closed form can be a compound of Formula I or Formula II:

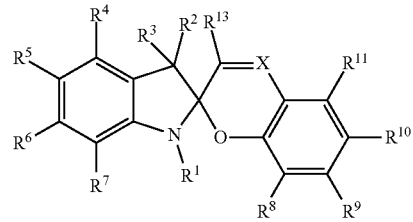

Formula I

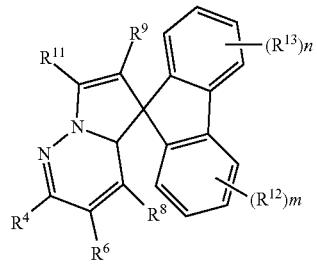

Formula II or a salt thereof, wherein the variables are as described herein.

The photochromic compound can have one or more functional groups suitable for attachment to a polymer. The photochromic compound can provide the ear tip with improved grip. Examples of photochromic compound include:
1'-(2-Hydroxyethyl)-3,3'-dimethyl-6-nitrospiro[1(2H)-benzopyran-2,2'-indoline];
1',3',3'-Trimethylspiro[1(2H)-benzopyran-2,2'-indoline];
1',3',3'-Trimethyl-6-nitrospiro[1(2H)-benzopyran-2,2'-indoline];
6-Bromo-1',3',3'-trimethylspiro[1(2H)-benzopyran-2,2'-indoline];
8-Methoxy-1',3',3'-trimethylspiro[1(2H)-benzopyran-2,2'-indoline];
1,3,3-Trimethylspiro[indoline-2,3'-[3H]naphth[2,1-b]pyran];
1,3,3-Trimethylspiro[indoline-2,3'-[3H]naphth[2,1-b][1,4]oxazine];
1',3'-dihydro-8-methoxy-1',3',3'-trimethyl-6-nitrospiro[2H-1-benzopyran-2,2'-(2H)-indole]; or
trimethyl 4a'H-spiro[fluorene-9,5'-pyrrolo[1,2-b]pyridazine]-3',6',7'-tricarboxylate;
or a salt thereof.

In some examples, the ear tip is connected to an earpiece comprising a light-emitting diode (LED), wherein the LED delivers light that causes the photochromic compound to convert to its zwitterion form, e.g., its open form.

In another aspect, the outer surface of the ear tip is coated with fibers, formed through electrostatic flocking. The fiber can be chop fiber, crimp fiber, fibrillated fiber, or a combination thereof. In some examples, the fiber includes polyacrylic, polyamide, polylactic acid, polyester, polyethylene, polypropylene, or cellulose, or a mixture thereof. The outer surface coated with fibers can be further coated with one or more photochromic compound that is a zwitterion in its open form.

All examples and features mentioned above can be combined in any technically possible way. Other features and advantages will be apparent from the description and the claims.

BRIEF DESCRIPTION OF THE DRAWINGS

FIG. 4A shows a mussel anchored by byssal threads and plaques to a rock in intertidal zone (Goleta Pier California). FIG. 4B shows a schematic of the distribution of different mfps in a plaque. FIG. 4C shows a primary sequence of mpf-5; S denotes phosphoserine. FIG. 4D shows a pie chart of key functionalities in mpf-5. FIG. 4E shows an example (Z-Cat-C10) of a zwitterionic surfactant inspired by mfp-5. FIG. 4F shows a light micrograph image of liquid-phase-separated Z-Cat-C10 at 100 mg ml-1 concentration.

DESCRIPTION

Figure 1:
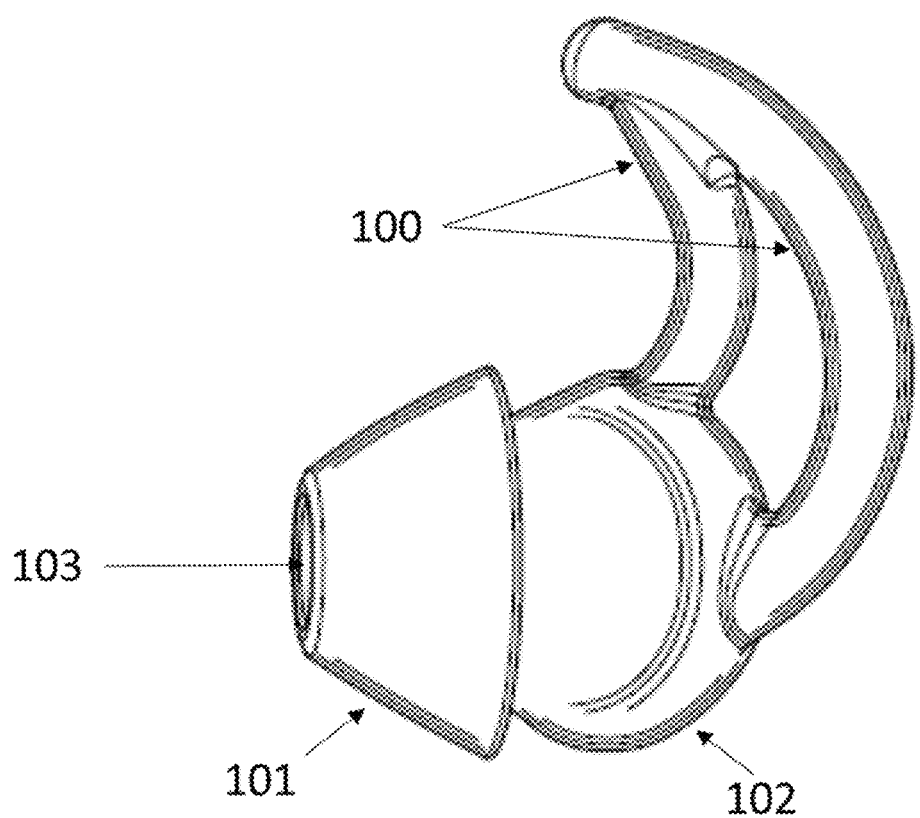
FIG. 1 shows a side view of an exemplary earpiece.
Figure 2:
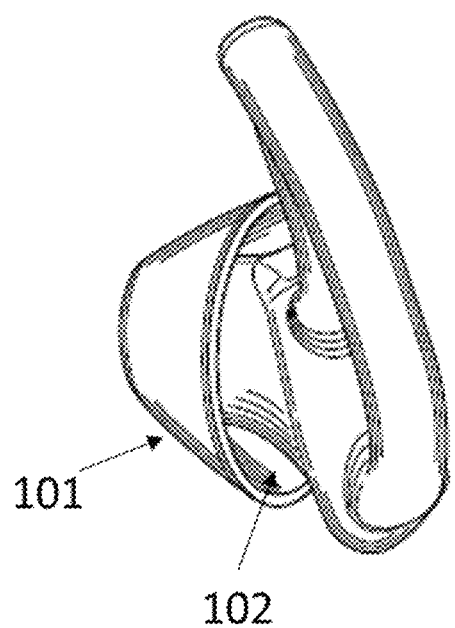
FIG. 2 shows a back view of the earpiece in FIG. 1.
Figure 3:
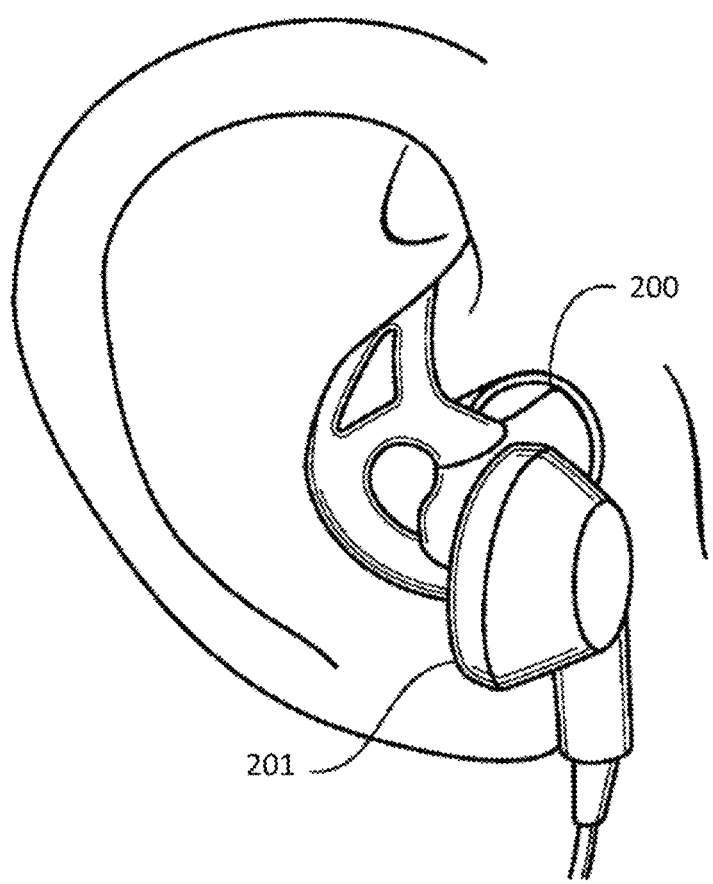
FIG. 3 shows an example of a headphone with an earpiece.

This application describes materials and processes for making apparatus such as wearable devices, more specifically headphone ear tips, with materials that can increase the amount of adhesion they exhibit towards skin when in use. Typically, an earpiece includes a tip that fits into the ear canal, and a retaining structure that is configured to hold the tip in place. FIG. 1 and FIG. 2 provide an exemplary earpiece showing retaining legs 100, tip 101, body 102, and a channel 103 that allows for conducting sound waves. The retaining legs are optional. An earpiece can be configured to be part of a headphone, which typically includes, at minimum, an acoustic driver module. FIG. 3 shows an example of a headphone with an earpiece 200 and acoustic driver module 201. Some earpieces may be connected to an audio generation device wirelessly via a BLUETOOTH® transceiver installed within the earpiece. Some earpieces may serve as passive earplugs that lack any connections or acoustic features. The ear tip can be made from a composition that includes an elastomer. Typical examples of elastomer used in ear tip includes silicone, polynorbornene, fluoroelastomer, styrenic-based thermoplastic elastomer, polyacrylates, hydrogenated nitrile rubber, or shape-memory polymers (e.g., polyurethane), or a mixture thereof. As described herein, the left and right earpieces may mirror each other, but have the same structure and function, or a symmetric earpiece may fit either ear.

Stability of ear tips in-ear can be problematic, particularly during sleep and sport activities. Improving the stability of ear tips improves overall comfort. Many methods to improve stability exist, from mechanical/design changes to material modifications. In the latter field, methods include top coats (e.g., spray, dip, paint, deposit) that provide a desired coefficient of friction (COF), different from uncoated silicone; micro- and nano-surface features such as gecko toe pads (Nanogriptech), micropillars (Microfingers, from 3M); and silicone suction cups (Inventibles). These features can either be built perpendicular to the surface or on angled wedges. All of these methods result in a common solution, a permanent change in COF. COF change is advantageous to improve stability, but can lead to insertion difficulties. Similar problems are presented in wearables other than in-ear headphones. That is, any wearable that is intended to have skin contact, such as a heart rate monitor, may need to balance the need to stay in place against comfort or an ability to be positioned accurately.

Instead of seeking to identify a single, optimized COF that covers both ease of insertion or positioning and improved stability needs, smart materials can be used to create wearable devices such as an ear tip that can change its properties in response to changes in the environment. By controlling those changes or arranging that they coincide with use of the headphones, a "turn on" and "turn off" style adhesive tip is provided herein. The tip is in the "off" state during insertion, and an environmental change such as temperature, pH, light, etc., triggers a change in the material, turning it "on" and rendering it grippy, that is, increasing its tendency to grip other materials, whether that be through friction, adhesion, or other properties. To remove, the tip is simply turned back "off" by removing or reverting the environmental stimulus that activated it. Similarly, a smart watch or other wearable devices may have a silicone contact pad that is non-grippy when being put on, but made grippy once positioned so that it stays in place. In some examples, the grippiness may be high enough that a wearable device may need no other attachment. That is, a pad may simply be placed on the skin, and activated to stay in place. When deactivated, the wearable device simply falls off.

Scheme 1 illustrates several mechanisms by which smart materials are triggered, and the resulting changes in chemical structure.

Scheme 1

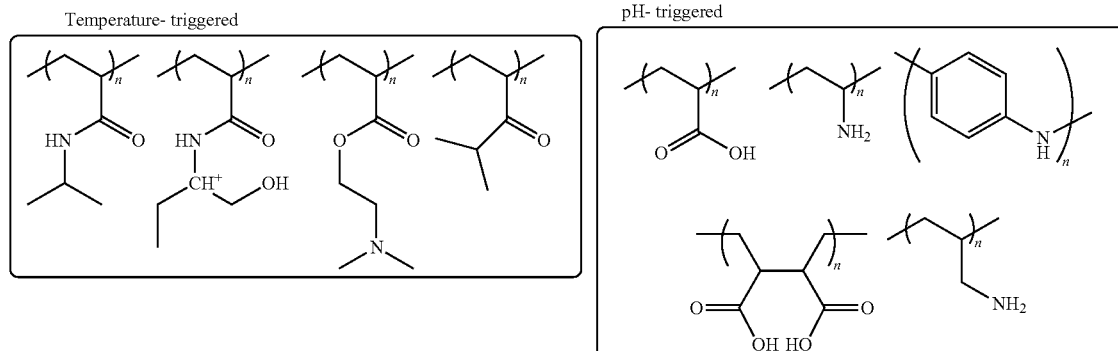

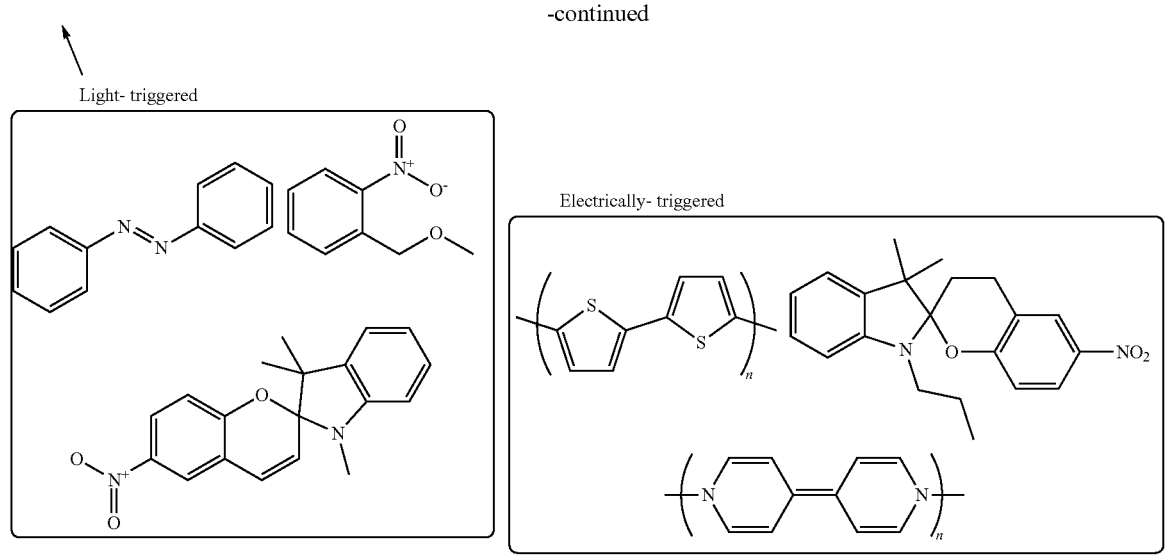

The four examples in Scheme 1 are temperature, pH, light, and electric charge. With temperature, the change may be artificially triggered outside of the ear during hot days, making insertion difficult. With electric charge, parasitic power consumption from the device would be a concern. It would be difficult to modify pH in a consumer product. Light is desirable for use in headphones. Using ultraviolet (UV) light to cure custom-shaped ear tips have previously been reported, see U.S. Provisional Patent Application 62/325,703 and its corresponding U.S. Non-provisional Publication 2017/0311069, both of which are incorporated here by reference. It would be advantageous, e.g., from a product cost and design point of view, to use the UV light source for additional functions.

Figure 4:
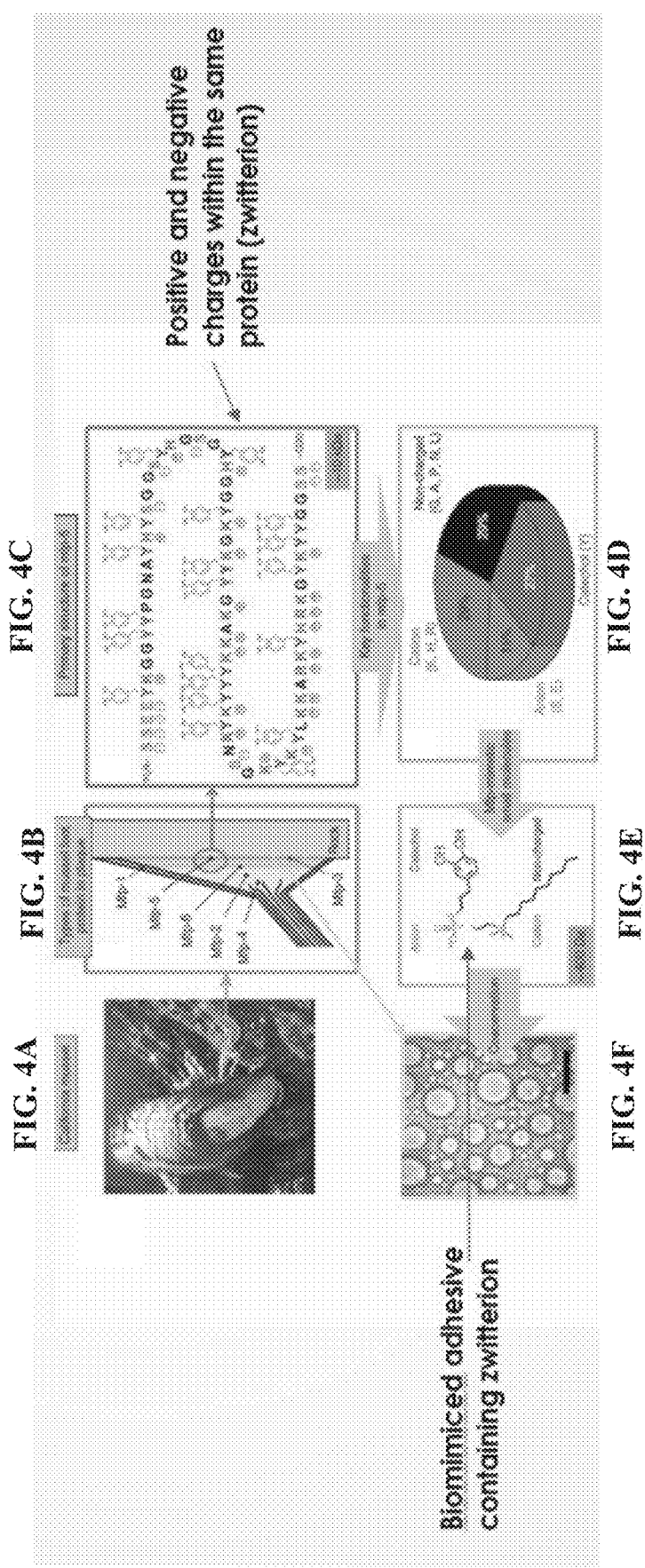
FIGS. 4A-4F show an example of zwitterions used in nature for the purpose of improved adhesion.

Dry adhesives such as gecko toe pads rely on two factors. First, a high degree of electrostatic interactions exist between the two surfaces in contact. Second, contact between the surfaces is split into finer subcontacts. Adhesion can be increased by introducing a strong dipole in a material in conjunction with or independent from microfeatures. One such approach is to utilize zwitterions. These dipolar ions are known to be strong adhesives in nature. See *Catecholic zwitterion as a biomimiced mussel adhesive for dry and wet environments*, Nature Communications, 6:8663, DOI: 10.1038/ncomms9663, and see FIG. 4, which is reproduced therefrom. In particular, photochromic compound such as spiropyran is a light activated zwitterion. Exposure to UV light leads to the ring opening, creating a dipole. Exposure to visible light reverts the molecule back to its uncharged state. See Scheme 2 (reproduced from *Chem. Mater.*, 2014, 26 (15), pp 4330-4333).

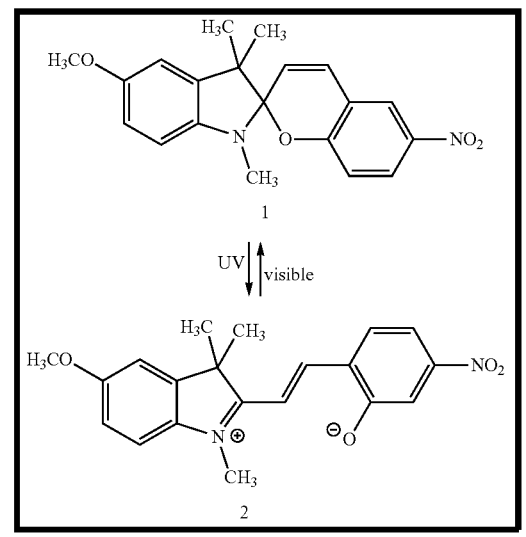

Scheme 2 shows the photo-induced ring-opening and ring-closing of the photochromic spiropyran (1) and merocyanine (2).

Provided herein is an apparatus such as a wearable device (e.g., ear tips for use in headphones) with increased adhesion to the user's skin. For example, the outer surface of an ear tip of a headphone can be coated with hierarchical microstructures that formed through chemical vapor deposition. The microstructures can be coated with a photochromic compound that is a zwitterion in its open form. Alternatively, the outer surface of the ear tip can be coated with a photochromic compound that is a zwitterion in its open form. The ear tip can also be made from a composition comprising a photochromic compound that is a zwitterion in its open form. Further, the outer surface can be coated with fibers, formed through electrostatic flocking. The wearable device can include any combination of features described herein. Provided herein are also methods of forming a wearable device (e.g., ear tip for use with a headphone) with any of the features described herein. Each of these features are described below.

Photochromic Compounds

Photochromic compounds have the ability to break and regenerate bonds, e.g., the breakage of the C—O bond of a spiropyran with irradiation, and this ability is responsible for the dynamic photochromic and tacky properties of spiropyran. It has been reported that spiropyran doped silicones (uniformly dispersed) showed a decrease in contact angle when triggered and a ~20% increase in adhesion compared with neat silicone at low loadings (0.25 wt %) (see e.g., *Chem. Mater.* 2014, 26, 4330-4333). Spiropyran as an adhesive, for example, spiropyran conjugated nanoparticles for controlling cell adhesion/detachment with exposure to different wavelengths of light, has also been studied (see e.g., *J. Am. Chem. Soc.* 2015, 137, 8199-8205). Further, salt-responsive zwitterionic polymer brushes with tunable friction and antifouling properties are examples of alternative triggers (see e.g., *Langmuir*, 2015, 31 (33), pp 9125-9133).

The outer surface of the ear tip described herein can be coated with a photochromic compound that is a zwitterion in its open form, and the ear tip can be made from a composition that includes a photochromic compound that is the same or different photochromic compound than the one coated on the surface of the ear tip. An earphone can be configured to mate with the ear tip, the source of applied energy including a light-emitting diode (LED) located in the earphone. The LED can be directly coupled to the inner wall of the ear tip (see e.g., U.S. Publication No. 2017-0311069). The LED can deliver light in the UV spectrum (350-365 nm) that causes the photochromic compound to convert to its zwitterion form. The tip would be inserted into the ear. The LED could be triggered externally, through a switch, or remotely, delivering UV light, causing a ring opening reaction and the formation of a zwitterion. This would improve adhesion to the skin. To remove the ear tip, the user could pull it out, where the zwitterion would revert to its lowest energy state upon exposure to visible light, or trigger the light source to deliver in the visible spectrum (550 nm).

The compound can include an indoline and a chromene moiety bound together via a Spiro junction and oriented perpendicular with respect to one another. Spiropyran-based dynamic materials are reported in the literature (see. e.g., Chem. Soc. Rev., 2014, 43, 148-184). The spiropyran moiety can be compatible with polymerization conditions; therefore, routes based on both polymerization of spiropyran-based monomers and grafting on pre-formed polymer chains have been employed. The grafting-on approach has been used to functionalize a variety of polymers, including polytetrafluoroethylene (PTFE; see e.g., D. J. Chung, et al., *J. Appl. Polym. Sci.*, 1994, 51, 2027-2033); polyaniline (see Y. Bardavid, et al., *J. Phys. Chem. C*, 2011, 115, 3123-3128); polyacrylates (see e.g., M. Moniruzzaman, et al., *Polymer*, 2007, 48, 255-263; Y. Bardavid, et al., *J. Phys. Chem. C*, 2011, 115, 3123-3128); polysulfones (e.g., J. Ratner, et al., *Ind. Eng. Chem. Res.*, 1996, 35, 1307-1315; A. Warshawsky, et al., *Ind. Eng. Chem. Res.*, 1995, 34, 2825-2832); polyphosphazenes (see e.g., H. R. Allcock et al., *Macromolecules*, 1991, 24, 2846-2851) and pluronics (e.g., Y. J. Oh, et al., *Macromol. Rapid Commun.*, 2012, 33, 1958-1963); homopolymers are typically synthesized by means of ring-opening metathesis polymerization (ROMP; see e.g., L. Hauser, et al., Monatsh. Chem., 2012, 143, 1551-1558; S. R. Keum, et al., Dyes Pigm., 2010, 86, 74-80).

Examples of photochromic compounds include spiropyran, spirooxazine, and spirodihydroindolizine. For example, the compound in its closed form can be a compound of Formula I or Formula II:

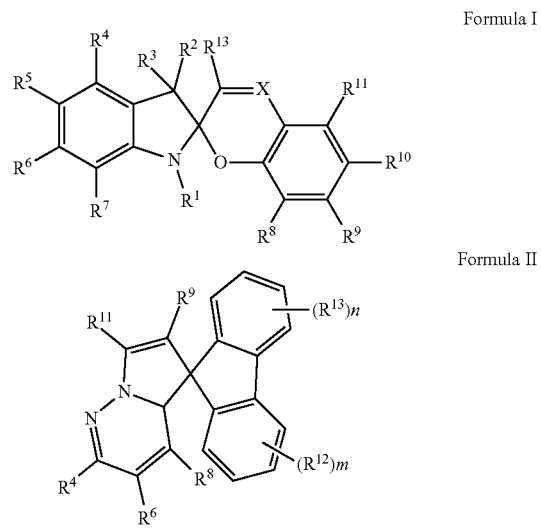

Formula I

Formula II or a salt thereof, wherein:

X is N or $CR^{12}$;

$R^1$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, and halo; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from halo, CN, OH, $NO_2$, CN, halo, $C_{1-6}$alkoxy, $C_{1-6}$haloalkoxy, amino, $C_{1-6}$ alkylamino, and di($C_{1-6}$alkyl)amino;

$R^2$, $R^3$, $R^4$, $R^6$, $R^7$, $R^8$, $R^9$, $R^{11}$, $R^{12}$ and $R^{13}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from halo, CN, OH, $NO_2$, CN, halo, $C_{1-6}$alkoxy, $C_{1-6}$haloalkoxy, amino, $C_{1-6}$ alkylamino, and di($C_{1-6}$ alkyl) amino;

$R^5$ is selected from H, $OR^{a2}$, $NR^{a2}R^{b2}$, OH, $NHCOR^{a2}$, and $OCOR^{a2}$;

$R^{10}$ is selected from H, $NO_2$, $SO_2CF_3$, $CF_3$, $CCl_3$, CN, $SO_3H$, CHO, $COR^{a3}$, COOH, COCl, $COOR^{a3}$, $CONH_2$, and halo;

or $R^{10}$ and $R^{11}$ together can form a 6-10 membered aryl optionally substituted with 1 or 2 substituents selected from $NO_2$, $SO_2CF_3$, $CF_3$, $CCl_3$, CN, $SO_3H$, CHO, $COR^{a3}$, COOH, COCl, $COOR^{a3}$, $CONH_2$, and halo;

$R^{a1}$, $R^{b1}$, $R^{c1}$, $R^{d1}$, $R^{a2}$, $R^{b2}$, and $R^{a3}$ are each independently selected from H, $C_{1-6}$ alkyl, $C_{2-6}$ alkenyl, $C_{2-6}$ alkynyl, and $C_{1-6}$ haloalkyl;

m is 0, 1, 2, 3, or 4; and n is 0, 1, 2, 3, or 4.

The photochromic compound can have one or more functional groups (e.g., hydroxyl groups) that are suitable for attachment to a polymer such as via a covalent bond. The zwitterion moieties can be also grafted onto silicone (see e.g., *Photochem. Photobiol. Sci.*, 2010, 9, 162-171).

Variable X can be N. X can be $CR^{12}$, e.g., CH.

$R^1$ can be selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, or 3 substituents independently selected from halo, CN, OH, $NO_2$, CN, halo, $C_{1-6}$ alkoxy, $C_{1-6}$ haloalkoxy, amino, $C_{1-6}$ alkylamino, and di($C_{1-6}$ alkyl)amino. In some examples, $R^1$ is $C_{1-6}$ alkyl optionally substituted with 1, 2, or 3 substituents independently selected from halo, CN, OH, $NO_2$, CN, halo, $C_{1-6}$ alkoxy, $C_{1-6}$ haloalkoxy, amino, $C_{1-6}$ alkylamino, and di($C_{1-6}$ alkyl)amino. For examples, $R^1$ can be methyl, ethyl, methoxy, or hydroxyethyl. In some examples, R' is methyl.

Variables $R^2$, $R^3$, $R^4$, $R^6$, $R^7$, $R^8$, $R^9$, $R^{11}$, $R^{12}$ and $R^{13}$ can each be independently selected from H, $C_{1-6}$ alkyl, $C_{2-6}$ alkenyl, $C_{2-6}$ alkynyl, $C_{1-6}$ haloalkyl, and halo, wherein said $C_{1-6}$ alkyl, $C_{2-6}$ alkenyl, and $C_{2-6}$ alkynyl are each optionally substituted with 1, 2, or 3 substituents independently selected from halo, CN, OH, $NO_2$, CN, halo, $C_{1-6}$ alkoxy, $C_{1-6}$ haloalkoxy, amino, $C_{1-6}$ alkylamino, and di($C_{1-6}$ alkyl) amino. Variables $R^2$, $R^3$, $R^4$, $R^6$, $R^7$, $R^8$, $R^9$, $R^{11}$, $R^{12}$ and $R^{13}$ can each be independently selected from H and $C_{1-6}$ alkyl. For examples, $R^2$, $R^3$, $R^4$, $R^6$, $R^7$, $R^8$, $R^9$, $R^{11}$, $R^{12}$ and $R^{13}$ are H.

$R^5$ can be selected from a electron-donating group. $R^5$ can be H, $OR^{a2}$ or OH. In some examples, $R^5$ is H. In other examples, $R^5$ is methoxy or ethoxy.

$R^{10}$ can be selected from a electron-withdrawing group. $R^{10}$ can be H, $NO_2$ or halo (e.g., F, Cl, Br, or I). In some examples $R^{10}$ is $NO_2$. In other examples, $R^{10}$ is halo (e.g., Br). Yet in some examples, $R^{10}$ is H.

Examples of photochromic compounds include the compounds shown in the table below or a salt thereof:

| Structure | Chemical name |
|---|---|
| 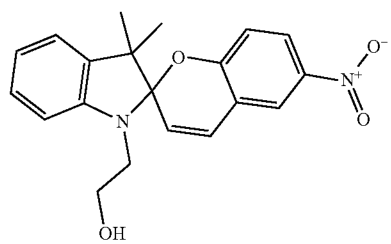 [SMILES: CC1(C)c2ccccc2N(CCO)C12C=Cc1cc([N+](=O)[O-])ccc1O2] | 1'-(2-Hydroxyethyl)-3',3'-dimethyl-6-nitrospiro[1(2H)-benzopyran-2,2'-indoline] |
| 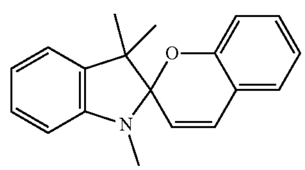 [SMILES: CN1c2ccccc2C(C)(C)C12C=Cc1ccccc1O2] | 1',3',3'-Trimethylspiro[1(2H)-benzopyran-2,2'-indoline] |
| 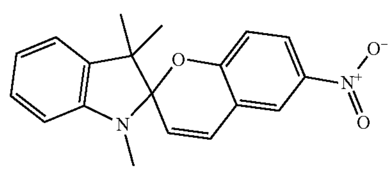 [SMILES: CN1c2ccccc2C(C)(C)C12C=Cc1cc([N+](=O)[O-])ccc1O2] | 1',3',3'-Trimethyl-6-nitrospiro[1(2H)-benzopyran-2,2'-indoline] |
| 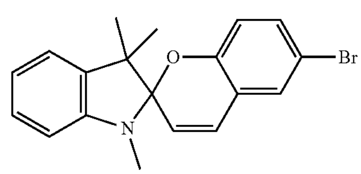 [SMILES: CN1c2ccccc2C(C)(C)C12C=Cc1cc(Br)ccc1O2] | 6-Bromo-1',3',3'-trimethylspiro[1(2H)-benzopyran-2,2'-indoline] |
| 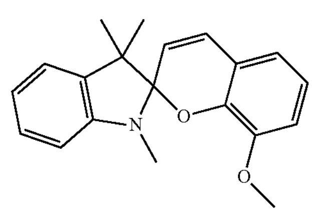 [SMILES: COc1cccc2c1OC1(C=C2)N(C)c2ccccc2C1(C)C] | 8-Methoxy-1',3',3'-trimethylspiro[1(2H)-benzopyran-2,2'-indoline] |

-continued

| Structure | Chemical name |
|---|---|
| 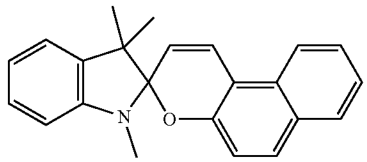 [SMILES: CN1c2ccccc2C(C)(C)C12C=Cc1c(ccc3ccccc13)O2] | 1,3,3-Trimethylspiro[indoline-2,3'-[3H]naphth[2,1-b]pyran] |
| 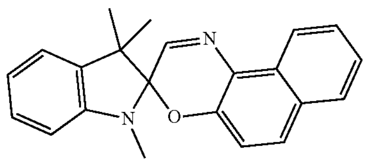 [SMILES: CN1c2ccccc2C(C)(C)C12C=Nc1c(ccc3ccccc13)O2] | 1,3,3-Trimethylspiro[indoline-2,3'-[3H]naphth[2,1-b][1,4]oxazine] |
| 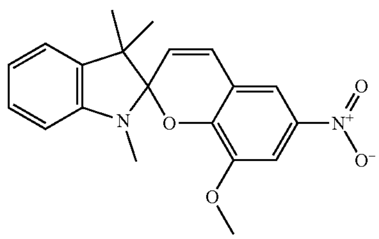 [SMILES: COc1cc([N+](=O)[O-])cc2c1OC1(C=C2)N(C)c2ccccc2C1(C)C] | 1',3'-dihydro-8-methoxy-1',3',3'-trimethyl-6-nitrospiro[2H-1-benzopyran-2,2'-(2H)-indole] |
| 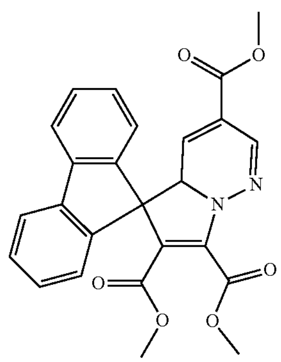 [SMILES: COC(=O)C1=CC2N(N=C1)C(C(=O)OC)=C(C(=O)OC)C21c2ccccc2-c2ccccc21] | trimethyl 4a'H-spiro[fluorene-9,5'-pyrrolo[1,2-b]pyridazine]-3',6',7'-tricarboxylate |

As an initial study, 1 wt % of spiropyran in silicone (Dragon Skin 30) was prepared. Spiropyran (from TCI chemicals (CAS 1498-88-0)) was hand mixed into part A of Dragon Skin 30 silicone (1 wt %), and the resulting mixture was mixed with part B of Dragon Skin 30 silicone at 1:1 ratio to part A. The mixed batch was degassed and casted to a film at 0.5 mm, and cured under at room temperature overnight.

Surface track measurements were conducted. Samples of the spiropyran/silicone were die cut into round coupons at a diameter of 2 cm, and wiped with acetone before measurement. Surface tack measurement was conducted using an AR 2000 ex rheometer (TA instruments), equipped with a UV curing accessory. The bottom of the samples is first glued to a UV transparent substrate. The stainless steel top tool is then used to compress the sample using a 30N load. The UV light is then triggered and the top tool is pulled off at a ramp rate of 50 um/sec. Surface tack was reported as the force measured to release the top plate from samples. A UV source below the bottom plate was used to trigger the dynamic transition of spiropyran molecules to induce the change in surface tackiness.

Figure 10:
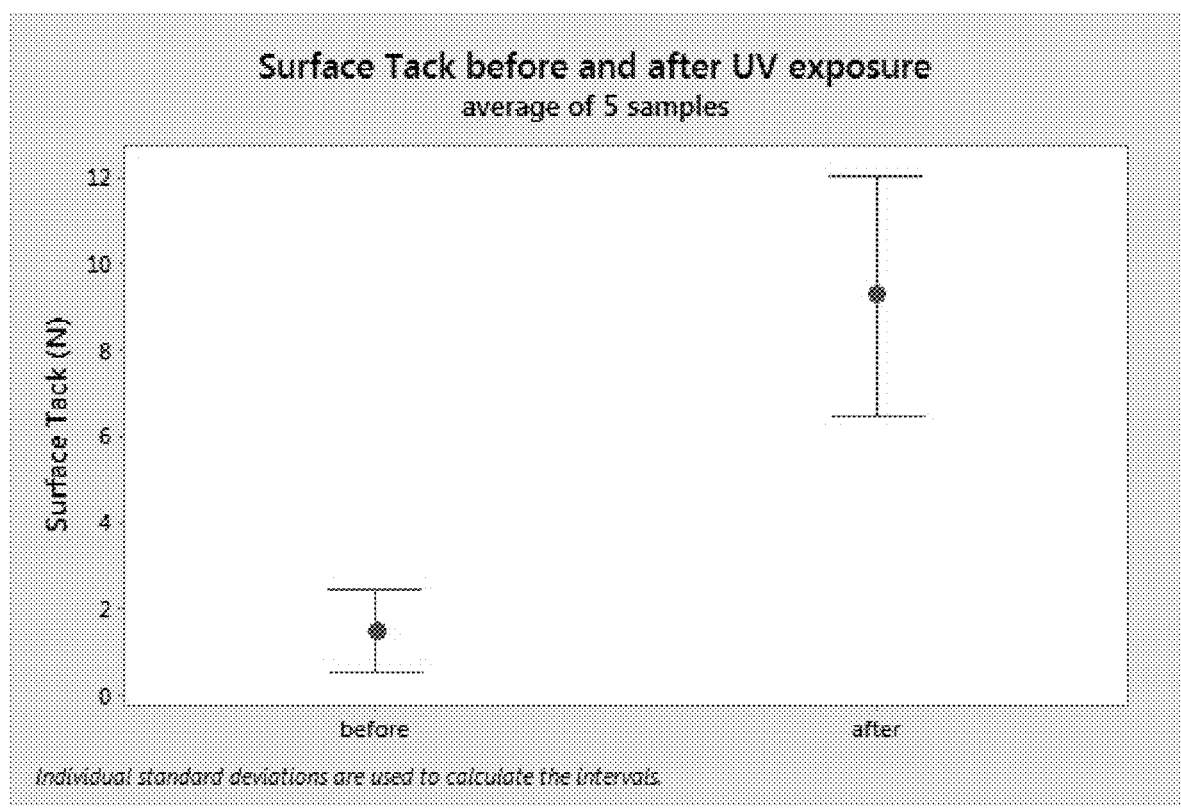
FIG. 10 shows a graph of surface tack measurement of a silicone sample incorporated with a spiropyran.

The data collected from the tack measurement on silicone incorporated with spiropyran (1',3',3'-Trimethyl-6-nitrospiro[1(2H)-benzopyran-2,2'-indoline] from TCI chemicals (CAS 1498-88-0)) on five samples show that surface tackiness was dramatically increased after UV exposure. See FIG. 10. Without UV light or under ambient light condition, samples remained at a non-tacky state. This dynamic transformation was also reversible (data not shown).

Figure 5:
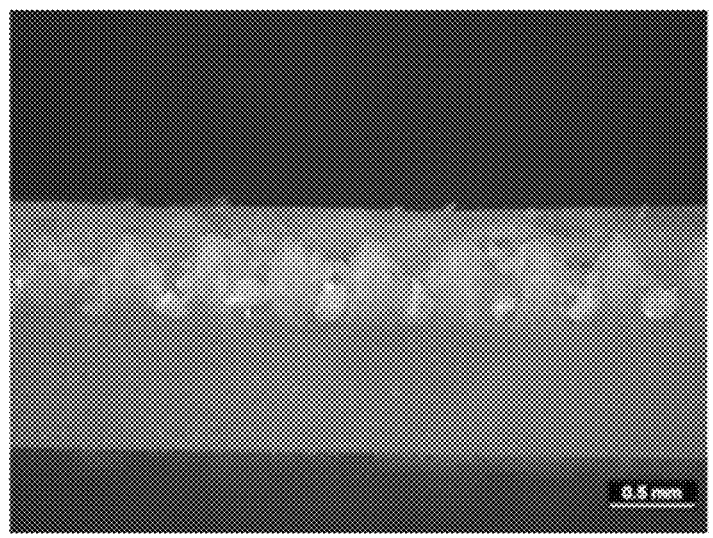
FIG. 5 is a magnified photograph of a material.

To increase the concentration of spiropyran at the surface that contacts a user's skin, a toothed structure is filled with spiropyran (from TCI chemicals (CAS 1498-88-0), and silicone is cast atop the filling to trap spiropyran into a matrix, see FIG. 5. This resulted in poor adhesion and encapsulation of the small molecule.

The term "$C_{n-m}$" indicates a range, where n and m are integers and indicate the number of carbons. Examples include $C_{1-4}$, $C_{1-6}$ and the like.

The term "alkyl" refers to a saturated hydrocarbon group that may be straight-chained or branched. The term "$C_{n-m}$ alkyl", refers to an alkyl group having n to m carbon atoms. An alkyl group corresponds to an alkane with one C—H bond replaced by the point of attachment of the alkyl group to the remainder of the compound. The alkyl group can contain from 1 to 6 carbon atoms, from 1 to 4 carbon atoms, from 1 to 3 carbon atoms, or 1 to 2 carbon atoms. Examples of alkyl moieties include chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" refers to a straight-chain or branched hydrocarbon group corresponding to an alkyl group having one or more double carbon-carbon bonds. An alkenyl group corresponds to an alkene with one C—H bond replaced by the point of attachment of the alkenyl group to the remainder of the compound. The term "$C_{n-m}$ alkenyl" refers to an alkenyl group having n to m carbons. The alkenyl moiety can contain 2 to 6, 2 to 4, or 2 to 3 carbon atoms. Example alkenyl groups include ethenyl, n-propenyl, isopropenyl, n-butenyl, sec-butenyl and the like.

The term "alkynyl" refers to a straight-chain or branched hydrocarbon group corresponding to an alkyl group having one or more triple carbon-carbon bonds. An alkynyl group corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include ethynyl, propyn-1-yl, propyn-2-yl and the like. In some embodiments, the alkynyl moiety contains 2 to 6, 2 to 4, or 2 to 3 carbon atoms.

The term "alkoxy" refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like.

The term "amino" refers to a group of formula —$NH_2$.

The terms "halo" or "halogen" refers to fluoro, chloro, bromo and iodo.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. Example haloalkyl groups include $CF_3$, $C_2F_5$, $CHF_2$, $CH_2F$, $CCl_3$, $CHCl_2$, $C_2Cl_5$ and the like.

The term "aromatic" refers to a carbocycle or heterocycle having one or more polyunsaturated rings having aromatic character (i.e., having (4n+2) delocalized π (pi) electrons where n is an integer).

The term "aryl," refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like.

The term "heteroaryl" or "heteroaromatic," refers to a monocyclic or polycyclic aromatic heterocycle having at least one heteroatom ring member selected from sulfur, oxygen and nitrogen. Any ring-forming N in a heteroaryl moiety can be an N-oxide. Example heteroaryl groups include pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl, indolyl, isoindolyl, and the like.

The term "cycloalkyl," refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Ring-forming carbon atoms of a cycloalkyl group can be optionally oxidized to form an oxo or sulfido group. Examples of cycloalkyl include cyclopropyl, cyclobutyl, cyclopentyl and cyclohexyl.

The term "heterocycloalkyl," refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Heterocycloalkyl groups can include mono- or bicyclic (e.g., having two fused or bridged rings) or spirocyclic ring systems. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. Examples of heterocycloalkyl groups include pyrrolidinyl; morpholino; azetidinyl; piperidinyl; and piperazinyl.

Dry Adhesives

Figure 9:
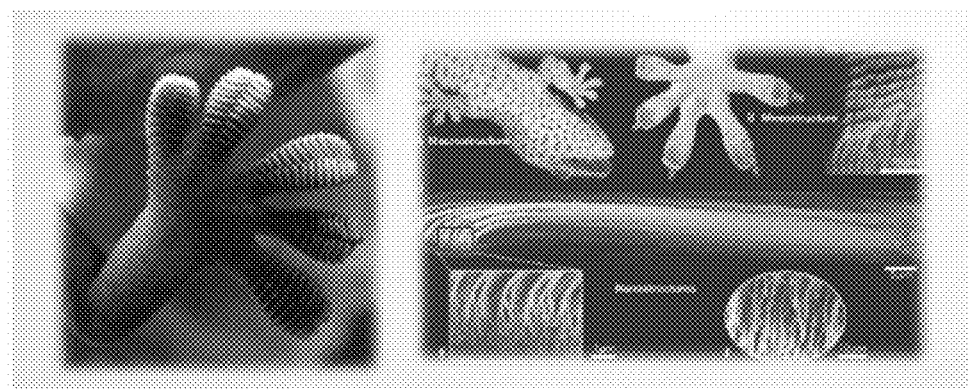
FIG. 9 shows Gecko footpads and electron micrographs of the same.

Another method to increase adhesion is dry adhesion, such as the toe pads of geckos, skinks, and anoline lizards, an example of which is shown in FIG. 9. Geckos' toe pads exhibit high adhesion in shear modes, and low adhesion in peel modes. This may be useful in headphone ear tips and other wearables even without the controlled activation (e.g., UV activation of photochromic compounds described above). During insertion and removal, and particularly intentional removal, the mode of interaction between the ear tip surface and skin can be peeling, while during use, the main mode of interaction is shear.

The adhesive properties of the gecko toe pads rely on two factors: a high degree of electrostatic interaction between the two surfaces in contact (animal and object), and contact between the surfaces being split into finer sub-contacts. The toe pads, as seen in the electron micrographs of FIG. 9, sub-divide into increasingly finer structures. Attempts to mimic this in synthetic materials, i.e., biomimicry, include basic stalks, stalks with shaped tips, angled features, and a hierarchy of structures.

It is difficult to manufacture such structures on an ear tip. Casting such fine structures is not generally feasible, as it is generally difficult to generate hierarchical structures in complex parts, especially at the micro- or nanometer scale as desired. Photolithography may work, but scalability is a challenge, as are curved surfaces. Additive manufacturing, including 3D printing and chemical vapor deposition (CVD) are two options. CVD is scalable, and can be used to grow complex structures.

A further advantage of using a "forest" of fine structures may be humidity control. Long-term wear of ear tips can create humidity buildup inside the ear canal, and particularly between the flesh and the ear tip material. A brush-like structure can allow vapor to escape the ear, while still providing positive retention and noise isolation with less spring-back force applied to the flesh than other designs, such as a deforming, umbrella-shaped or mushroom-shaped tip.

Figure 7:
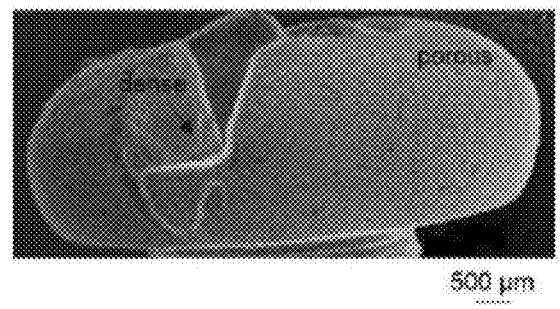
FIG. 7 and FIG. 8 show electron micrographs of coated objects.
Figure 8:
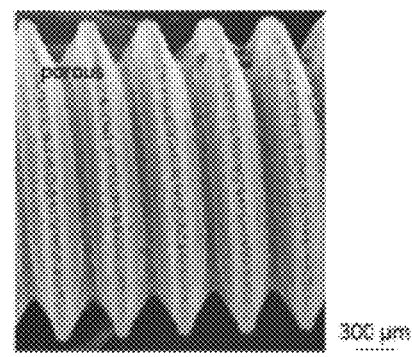

To increase the adhesion or grippiness of an ear tip, the outer surface of the ear tip that contacts the body of a user can be coated with hierarchical microstructures. The microstructures can be formed through chemical vapor deposition and mimic the structures of gecko toe pads, which are known to have fine microstructures that make them adhere to surfaces. The microstructures formed through chemical vapor deposition can include a dense polymer and a porous polymer, see FIG. 7, FIG. 8, and FIG. 9. Detailed procedures are disclosed in *Macromol. Mater. Eng.* 2016, 301, 371-376; and *Macromol. Mater. Eng.* 2016, 301, 1037-1043.

The microstructures formed through CVD process can be incorporated onto the surface of the ear tip via an adhesive process, e.g., oxidation or chlorination of the surface. The oxidation process includes a Plasma Cleaner (PDC-32G). The chlorination process includes using an aqueous solution of sodium dichloroisocyanurate. These processes help mechanically and chemically attach microstructures to the surface. A tape test can be performed to qualitatively assess whether the microstructures have been adhered to the surface. In this test, a piece of tape is applied to the surface of the coated substrate. It is then removed and inspected for material transfer. It is desirable to have a lower transfer of the microstructures onto the tape.

Figure 6:
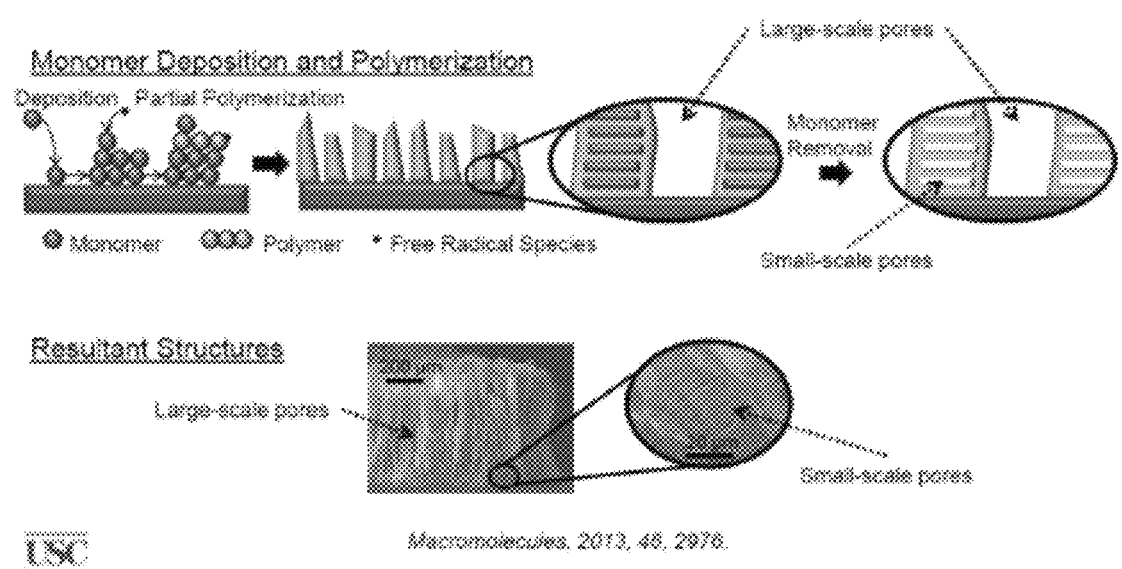
FIG. 6 shows a schematic diagram and an electron micrograph of monomer deposition and polymerization of certain materials.

The hierarchical microstructures on the outer surface of the ear tip can also be coated with a photochromic compound described herein. Alternatively, the photochromic compounds can be incorporated into a chemical vapor deposition (CVD) process, see *Macromolecules* 2013, 46, 2976, and FIG. 6, which is taken therefrom. The CVD can create various surface morphologies including gecko-like surfaces. This method has been used to coat complex shapes, see FIG. 7 and FIG. 8. Headphone ear tips coated with hierarchical microstructures where photochromic compounds have been incorporated either by coating on the microstructures or during the CVD process can have their COF or "grippiness" temporarily changed though the application of ultraviolet light as described above.

Electrostatic Flocking

Figure 11:
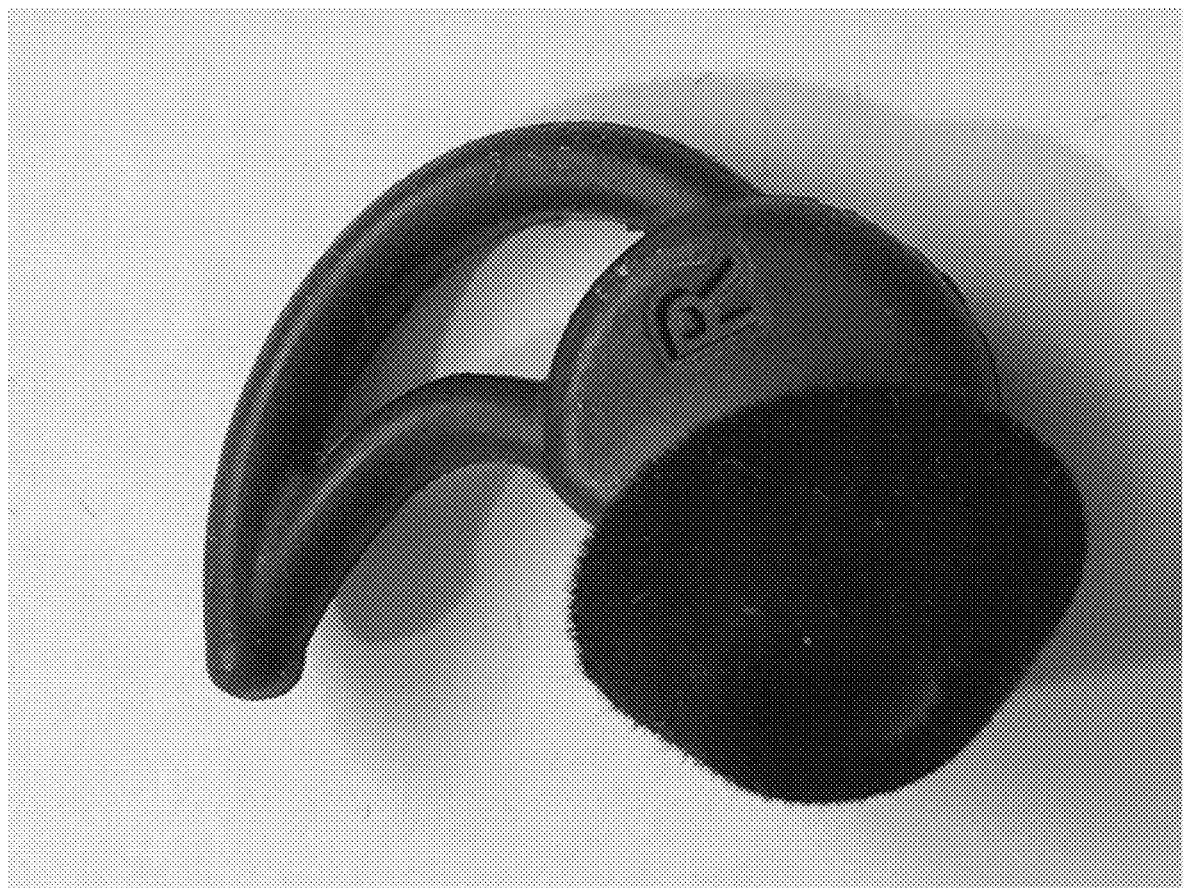
FIG. 11 shows an example of headphone ear tip coated with fibers.

This disclosure also includes increasing the surface of the wearable device such as the ear tip of headphones by coating such surfaces with fibers. The coated surface can be formed through electrostatic flocking. For example, Mecodur D282 Flex can be used as an adhesive to adhere the flocked fibers to the ear tip. Example of an ear tip coated w. 0.5 mm 1.7 dtex Nylon chopped fibers is shown in FIG. 11.

Examples of fiber include chop fiber, crimp fiber, fibrillated fiber, or a combination thereof. The fiber can be made from compositions that include polyacrylic, polyamide, polylactic acid, polyester, polyethylene, polypropylene, or cellulose, or a mixture thereof. The surface coated with the fibers can be further coated with one or more photochromic compounds described herein.

A number of implementations have been described. Nevertheless, it will be understood that additional modifications may be made without departing from the scope of the inventive concepts described herein, and, accordingly, other embodiments are within the scope of the following claims.

What is claimed is:

1. An apparatus comprising:
    a human-interface component of a wearable device having the form of an ear tip for use with a headphone, the component having an outer surface shaped to contact a portion of the body of a user, wherein:
    (i) the outer surface is coated with hierarchical microstructures, formed through chemical vapor deposition; wherein the microstructures are coated with a photochromic compound that is a zwitterion in its open form;
    (ii) the outer surface is coated with a photochromic compound that is a zwitterion in its open form;
    (iii) the component is made from a composition comprising a photochromic compound that is a zwitterion in its open form; or
    (iv) the outer surface is coated with fibers, formed through electrostatic flocking; wherein the surface coated with the fibers is further coated with one or more photochromic compound that is a zwitterion in its open form; or
    (v) any combination thereof;

wherein the ear tip comprises an elastomer, and the ear tip is connected to an earpiece comprising a light-emitting diode (LED), wherein the LED delivers light that causes the photochromic compound to convert to its zwitterion form.

2. The apparatus of claim 1, wherein the microstructures, photochromic compound, fibers, or a combination thereof, provide the outer surface of the component with increased adhesion.

3. The apparatus of claim 1, wherein the elastomer is silicone, polynorbornene, fluoroelastomer, styrenic-based thermoplastic elastomer, polyacrylates, hydrogenated nitrile rubber, or shape-memory polymers, or a mixture thereof.

4. The apparatus of claim 3, wherein the shape-memory polymer is polyurethane.

5. The apparatus of claim 1, wherein the outer surface of the ear tip is coated with hierarchical microstructures, formed through chemical vapor deposition; wherein the microstructures are coated with a photochromic compound that is a zwitterion in its open form.

6. The apparatus of claim 1, wherein the outer surface of the ear tip is coated with a photochromic compound that is a zwitterion in its open form.

7. The apparatus of claim 1, wherein the ear tip is made from a composition comprising a photochromic compound that is a zwitterion in its open form.

8. The apparatus of claim 7, wherein the outer surface of the ear tip is coated with a photochromic compound that is a zwitterion in its open form, wherein the photochromic compound on the outer surface is the same or different from the photochromic compound of the composition used to make the ear tip.

9. The apparatus of claim 1, wherein the photochromic compound is spiropyran, spirooxazine, or spirodihydroindolizine.

10. The apparatus of claim 1, wherein the photochromic compound in its closed form is a compound of Formula I or Formula II:

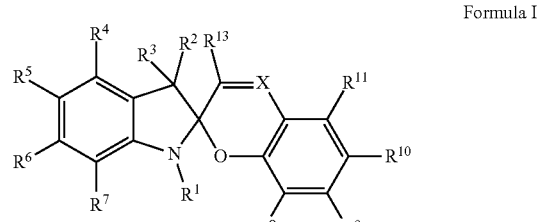

Formula I

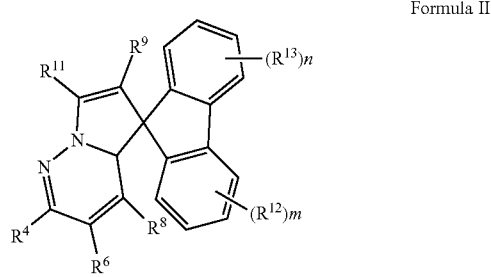

Formula II or a salt thereof, wherein:
X is N or $CR^{12}$;
$R^1$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, and halo; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from halo, CN, OH, $NO_2$, CN, halo, $C_{1-6}$ alkoxy, $C_{1-6}$ haloalkoxy, amino, $C_{1-6}$ alkylamino, and di($C_{1-6}$ alkyl)amino;

$R^2$, $R^3$, $R^4$, $R^6$, $R^7$, $R^8$, $R^9$, $R^{11}$, $R^{12}$ and $R^{13}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from halo, CN, OH, $NO_2$, CN, halo, $C_{1-6}$ alkoxy, $C_{1-6}$ haloalkoxy, amino, $C_{1-6}$ alkylamino, and di($C_{1-6}$ alkyl)amino;

$R^5$ is selected from H, $OR^{a2}$, $NR^{a2}R^{b2}$, OH, $NHCOR^{a2}$, and $OCOR^{a2}$;

$R^{10}$ is selected from H, $NO_2$, $SO_2CF_3$, $CF_3$, $CCl_3$, CN, $SO_3H$, CHO, $COR^{a3}$, COOH, COCl, $COOR^{a3}$, $CONH_2$, and halo;

or $R^{10}$ and $R^{11}$ together can form a 6-10 membered aryl optionally substituted with 1 or 2 substituents selected from $NO_2$, $SO_2CF_3$, $CF_3$, $CCl_3$, CN, $SO_3H$, CHO, $COR^{a3}$, COOH, COCl, $COOR^{a3}$, $CONH_2$, and halo;

$R^{a1}$, $R^{b1}$, $R^{c1}$, $R^{d1}$, $R^{a2}$, $R^{b2}$, and $R^{a1}$ are each independently selected from H, $C_{1-6}$ alkyl, $C_{2-6}$ alkenyl, $C_{2-6}$ alkynyl, and $C_{1-6}$ haloalkyl;

m is 0, 1, 2, 3, or 4; and n is 0, 1, 2, 3, or 4.

11. The apparatus of claim 1, wherein the photochromic compound has one or more functional groups suitable for attachment to a polymer.

12. The apparatus of claim 1, wherein the photochromic compound provides the ear tip with improved grip.

13. The apparatus of claim 1, wherein the photochromic compound is:
- 1'-(2-Hydroxyethyl)-3',3'-dimethyl-6-nitrospiro[1(2H)-benzopyran-2,2'-indoline];
- 1',3',3'-Trimethylspiro[1(2H)-benzopyran-2,2'-indoline];
- 1',3',3'-Trimethyl-6-nitrospiro[1(2H)-benzopyran-2,2'-indoline];
- 6-Bromo-1',3',3'-trimethylspiro[1(2H)-benzopyran-2,2'-indoline];
- 8-Methoxy-1',3',3'-trimethylspiro[1(2H)-benzopyran-2,2'-indoline];
- 1,3,3-Trimethylspiro[indoline-2,3'-[3H]naphth[2,1-b]pyran];
- 1,3,3-Trimethylspiro[indoline-2,3'-[3H]naphth[2,1-b][1,4]oxazine];
- 1',3'-dihydro-8-methoxy-1',3',3'-trimethyl-6-nitrospiro[2H-1-benzopyran-2,2'-(2H)-indole]; or
- trimethyl 4a'H-spiro[fluorene-9,5'-pyrrolo[1,2-b]pyridazine]-3',6',7'-tricarboxylate;

or a salt thereof.

14. The apparatus of claim 1, wherein the outer surface of the ear tip is coated with fibers, formed through electrostatic flocking, wherein the outer surface coated with fibers is further coated with one or more photochromic compound that is a zwitterion in its open form.

15. The apparatus of claim 14, wherein the fiber is chop fiber, crimp fiber, fibrillated fiber, or a combination thereof.

16. The apparatus of claim 14, wherein the fiber comprises polyacrylic, polyamide, polylactic acid, polyester, polyethylene, polypropylene, or cellulose, or a mixture thereof.

\* \* \* \* \*

UNITED STATES PATENT AND TRADEMARK OFFICE
CERTIFICATE OF CORRECTION

PATENT NO. : 10,506,326 B2
APPLICATION NO. : 15/967994
DATED : December 10, 2019
INVENTOR(S) : Shawn J. Prevoir and Kai Gao It is certified that error appears in the above-identified patent and that said Letters Patent is hereby corrected as shown below:

In the Claims

Column 17, Line 29, in Claim 10, delete "$R^{a1}$" and insert -- $R^{a3}$ --, therefor.

Signed and Sealed this
Tenth Day of March, 2020

Andrei Iancu
*Director of the United States Patent and Trademark Office*